US00PP25674P3

(12) United States Plant Patent
Brown

(10) Patent No.: US PP25,674 P3
(45) Date of Patent: Jul. 7, 2015

(54) ***WESTRINGIA* HYBRID PLANT NAMED 'WES03'**

(50) Latin Name: ***Westringia* hybrid**
Varietal Denomination: WES03

(71) Applicant: Graham Brown, Pennant Hills (AU)

(72) Inventor: Graham Brown, Pennant Hills (AU)

( * ) Notice: Subject to any disclaimer, the term of this patent is extended or adjusted under 35 U.S.C. 154(b) by 307 days.

(21) Appl. No.: 13/694,300

(22) Filed: Nov. 17, 2012

(65) Prior Publication Data

US 2014/0143920 P1 May 22, 2014

(51) Int. Cl.
*A01H 5/00* (2006.01)
*A01H 5/02* (2006.01)

(52) U.S. Cl.
USPC ..... Plt./226
CPC ..... *A01H 5/02* (2013.01)

(58) Field of Classification Search
USPC ..... Plt./226
CPC ..... A01H 5/00; A01H 5/02
See application file for complete search history.

*Primary Examiner* — Kent L Bell
(74) *Attorney, Agent, or Firm* — Samuel R. McCoy, Jr.

(57) ABSTRACT

'WES03' is a distinctive variety of *Westringia* hybrid which is characterized by an erect to semi erect shrub habit and vivid, deeply colored violet flowers.

2 Drawing Sheets

Latin name of the genus and species: The Latin name of the genus and species of the novel variety disclosed herein is *Westringia* hybrid.

Variety denomination: The inventive variety of *Westringia* hybrid disclosed herein has been given the variety denomination 'WES03'.

The present application claims priority from a provisional U.S. application Ser. No. 61/561,532 filed Nov. 18 2011, which is herein incorporated by reference.

BACKGROUND OF THE INVENTION

The present invention relates to a new and distinct perennial variety of hybrid *Westringia*, which has been given the variety denomination of 'WES03'. Its market class is that of an ornamental plant. 'WES03' is intended for use in landscaping and as a decorative plant.

Parentage: Controlled pollination of maternal parent *Westringia* hybrid 'x2003.9.1' (unpatented) with pollen parent *Westringia* hybrid 'x2003.9.3' (unpatented) in September of 2004 at a commercial plant breeding facility in Cobbity, New South Wales, Australia. Resulting seed was sown the following year in March 2005. Several seedlings were selected and subsequently transferred to 10 cm pots in October of 2005. The *Westringia* hybrid variety 'WES03' was finally selected in 2009 following a selection process carried out from 2005 to 2009. 'WES03' was selected for possessing uniquely colored flowers and upright yet shorter growth habit compared to both parents.

Asexual Reproduction: 'WES03' was first propagated asexually by division in the state of New South Wales, Australia and has since been asexually propagated by division and micropropagation. The distinctive characteristics of the inventive 'WES03' variety are stable from generation to generation; plants of the variety produced by asexual reproduction maintain the distinguishing characteristics of the original plant.

An application for plant breeders' rights for variety 'WES03' has been lodged with the Australian Plant Breeders' Rights Office, and was accepted on 13 May 2011 under Application No. 2011/044.

SUMMARY OF THE INVENTION

'WES03' is a distinctive variety of hybrid *Westringia* which is characterized by an erect to semi erect shrub habit and vivid, deeply colored violet flowers.

BOTANICAL DESCRIPTION OF THE PLANT

Figure 1:
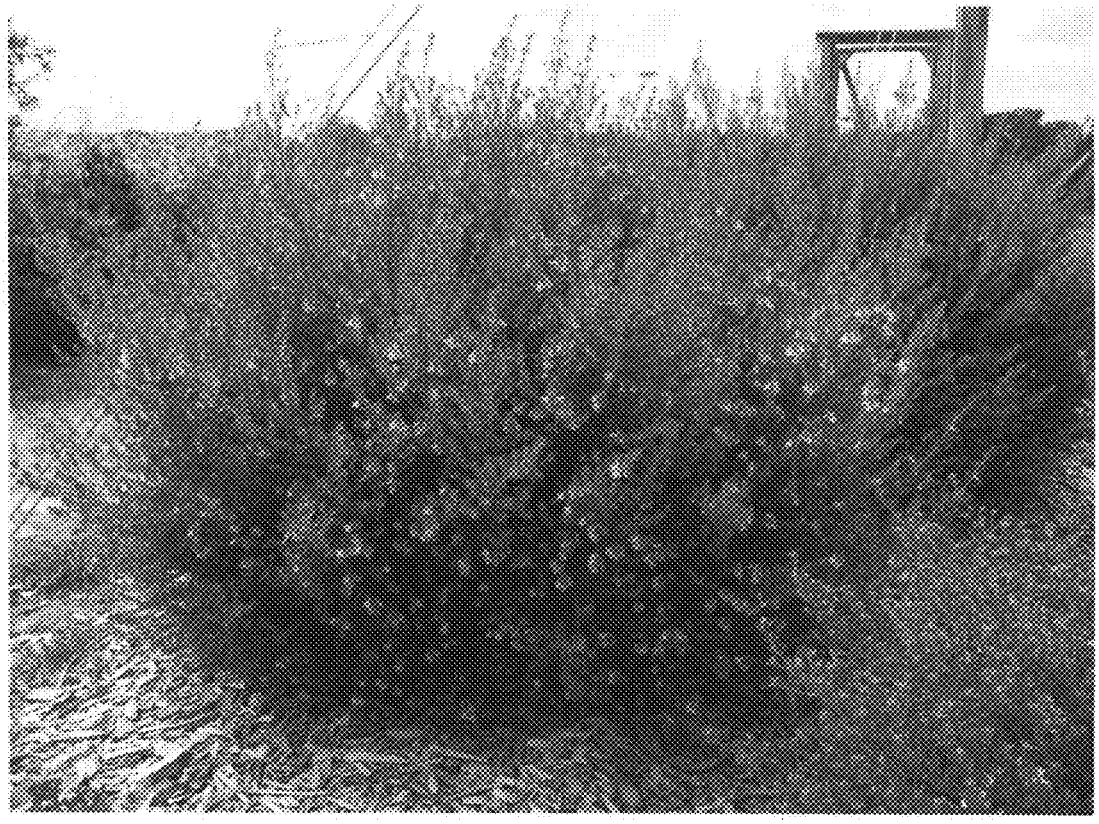
FIG. 1 illustrates a mature 'WES03' plant.
Figure 2:
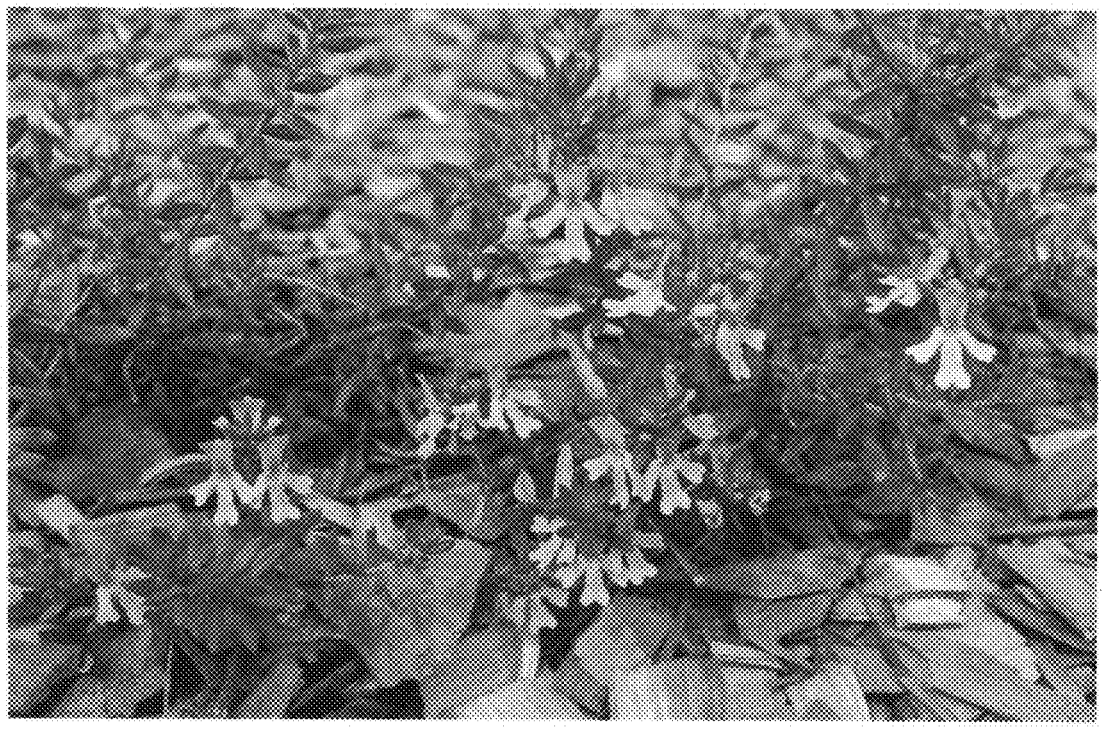
FIG. 2 illustrates the flower of a 'WES03' plant.

The following is a detailed botanical description of a new and distinct variety of a *Westringia* hybrid ornamental plant known as 'WES03'. Plant observations were made on plants grown from rooted cuttings into 10 inch nursery pots in Charleston, S.C. Unless indicated otherwise, the descriptions disclosed herein are based upon observations made from mature 'WES03' plants grown from rooted cuttings filled with soilless potting media, maintained with granular slow release fertilizer, and regularly watered with overhead irrigation. No pest and disease measures were taken. Observation data was recorded in October of 2011.

Those skilled in the art will appreciate that certain characteristics will vary with older or, conversely, younger plants. 'WES03' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural*

*Society Colour Chart*, The Royal Horticultural Society, London, 1986 edition. Note that generic color descriptions such as 'white' do not exist in the RHS charts and the corresponding RHS colors are quoted.

'WES03' is a perennial *Westringia* hybrid plant which is a seedling selection from hybrid *Westringia* parentage, both unpatented. After its selection, 'WES03' was asexually propagated by division. 'WES03' has an upright, shruby habit and vivid, deeply colored violet flowers. These features and other characteristics are apparent from the description provided below.

GROWTH HABIT, DIMENSIONS AND COLOR

Plant description:

*Bloom period*.—Spring with sporadic flowering in fall.
*Plant habit*.—Shrubby; upright, rounded and dense.
*Height*.—150 cm at maturity.
*Width*.—130 cm at maturity.
*Hardiness*.—USDA Zone 9 to 11.
*Propagation*.—Propagation is accomplished using softwood cuttings. Roots well without rooting compound or hormone.
*Time to develop roots*.—2 to 4 weeks
*Crop time*.—From four to six months are needed to produce a 14-centimeter container with plant in flower, starting from a rooted cutting.
*Pest and disease susceptibility or resistance*.—In common with the species, none of note.

Stem:

*Shape*.—Cylindrical yet angular.
*Stem color*.—Young stem is closest to green 138B.
*Stem dimensions*.—mature stem is approximately 35 cm in length with a diameter of 7 mm near the base.
*Stem surface*.—Corky.
*Basal stem color*.—Ranges from green 138B to grey 201C to 200A at maturity.
*Branching and habit*.—Strong branching habit; upright growth habit.
*Internode length*.—12 mm on average.

Foliage:

*Type*.—Evergreen.
*Shape*.—Elliptical, narrow.
*Division*.—Simple.
*Apex*.—Acute.
*Base*.—Cunneate.
*Venation*.—Pinnate.
*Vein color* (*adaxial surfaces*).—139A.
*Vein color* (*abaxial surfaces*).—138B.
*Margins*.—Entire.
*Arrangement*.—Whorled.
*Attachment*.—Petiolate.
*Texture*.—Leathery.
*Surfaces* (*adaxial surface*).—Finely pubescent to glabrous.
*Surfaces* (*abaxial surface*).—Heavily pubescent.
*Mature leaf dimensions*.—Average length 11.5 mm, average width 2.5 mm.
*Leaf color* (*adaxial surface*).—Juvenile: 138A; mature: 139A.
*Leaf color* (*abaxial surface*).—Juvenile: 138B; mature: 138B.
*Petiole*.—Approximately 1 to 2 mm in length; width minute; color is green (RHS 138 B).
*Stipules*.—Laminar and green (RHS 138A); pubescent; length is approximately 2 to 4 mm.

Inflorescence: Flowers are sessile, singular and persist for approximately 5 days. Self cleaning. Non fragrant.

*Flowers*.—Small; Sympetalous, irregular with sepal lobes appearing to number five, width across the corolla measuring on average 12.2 mm and a length of 15 mm (average); color approximates to 84A.
*Bud*.—Not yet described.
*Calyx*.—Synsepalous with five sepal lobes; basally fused; coroniform; inner surface color is green (RHS 137C) and the outer surface appearing as a combination of green (RHS 137C) and greyed-red (RHS 178A). The length of the calyx, including sepal lobes, is 6.5 mm and the width at the widest point across the calyx is 4.0 mm.
*Sepals*.—Sepal surfaces — Pubescent. Number of sepals — Five. Sepal shape — Lanceolate. Sepal apex — Acute. Sepal base — Fused. Sepal margin — Entire. Sepal dimensions — length is approximately 3.0 mm; width at the base is approximately 2.0 to 2.5 mm wide. Sepal color (inner surface) — Green (RHS 137C). Sepal color (outer surface) — A combination of green (RHS 137C) and greyed-red (RHS 178A).

Reproductive organs:

*Stamens*.—4.
*Stamen color*.—84A.
*Stamen dimensions*.—About 3 mm in length and very thin.
*Attachment*.—Each stamen joins floral tube independently: Free.
*Anther dimensions*.—Minute.
*Anther color*.—Yellow.
*Pollen*.—Absent.
*Pistil*.—One.
*Pistil dimensions*.—About 8 mm. in length and very thin.
*Pistil color*.—84A.
*Ovary position*.—Half-Inferior.

Fruit and seed production: Not yet observed

COMPARISON OF WES03 WITH OTHER VARIETIES OF HYBRID *WESTRINGIA*

When compared to both the seed and pollen parent, 'WES03' has a shorter plant height and a deep purple flower color whereas both parents possess a mauve colored flower.

'WES03' is similar in form and function to *Westringia* hybrid 'Wynyabbie Gem' in that both have an erect to semi erect shrub habit and both have a flower with color in the hue of violet. However 'WES03' has a flower that is a deeper hue of violet corresponding to RHS 84A whereas the flowers of 'Wynyabbie Gem' are a lighter hue of violet corresponding to RHS 85C. The flowers of 'WES03' are also slightly larger than 'Wynyabbie Gem'; the corolla of 'WES' is 15 mm (average) in length whereas 'Wynyabbie Gem' is approximately 10 mm in length. 'WES03' has small green leaves with an average length of 11.5 mm and a width of 2.5 mm whereas the leaves of 'Wynyabbie Gem' are grey green and larger with a length of up to 20 mm and a width of approximately 3 mm.

The combination of its deeper violet flowers, larger flowers and smaller leaves makes 'WES03' a desirable ornamental plant suited for mass production for pot and landscape use.

Which is claimed is:

1. A new and distinct variety of *Westringia* hybrid plant named 'WES03', substantially as described and illustrated herein.

* * * * *